US 6,500,409 B1
(10) Patent No.: US 6,500,409 B1
(45) Date of Patent: Dec. 31, 2002

(12) United States Patent
Scherl et al.

(54) SYNERGISTIC ANTIPLAQUE/ ANTIGINGIVITIS ORAL COMPOSITION

(75) Inventors: Dale S. Scherl, Somerset, NJ (US); Susan M. Herles, Flemington, NJ (US); Tao Xu, Newton, MA (US); Abdul Gaffar, Princeton, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/568,114

(22) Filed: May 10, 2000

(51) Int. Cl.⁷ .............................. A61K 7/26; A61K 7/16; A61K 35/78
(52) U.S. Cl. .................... 424/58; 424/49; 424/195.1
(58) Field of Search .......................... 424/49–58, 195.1

(56) References Cited

U.S. PATENT DOCUMENTS

| 4,537,996 A | * | 8/1985 | Kooda et al. | 568/442 |
| 5,032,386 A | * | 7/1991 | Gaffar et al. | 424/49 |
| 5,080,887 A | * | 1/1992 | Gaffar et al. | 424/52 |
| 5,135,746 A | * | 8/1992 | Matsuno et al. | 424/195.1 |
| 5,188,821 A | | 2/1993 | Gaffar et al. | 424/52 |
| 5,288,480 A | * | 2/1994 | Gaffar et al. | 424/52 |

FOREIGN PATENT DOCUMENTS

| CN | 1094895 A | * | 11/1994 | |
| CN | 1096699 A | * | 12/1994 | |
| JP | 57085319 A2 | * | 5/1982 | |
| JP | 01151512 A | * | 6/1989 | |
| JP | 10152426 A | * | 6/1998 | |
| JP | 2001010904 A | * | 1/2001 | |
| WO | 9735599 | | 10/1997 | ........... A61K/35/78 |

OTHER PUBLICATIONS

Ho Et Al Phyto Ther. Res. 15(2): 139–141 Honokiol/Magnolol MIC 25.Mu G/ml., 2001.*
Mao Et Al Zhongguo Gonggong Weisheng Xuebao 18(4): 215–216 H/M: MBC 16.Mu G/ml., 1999.*
Namba Et Al Wakanyaku Shinpojumu 15:179–186 M/H MIC 6.3 Mu G/ml, 1982.*
Namba Et Al Planta Med 44(2): 100–106 M/A : MIC 6.3 Mu G/ml., 1982.*
Namba Et Al Shoya Kugaku Zasshi 36(3):222–227 M/H : MIC 12.5.25Mug/m., 100 Mug/ml, 1982.*
Chang Et Al Planta Med 64(4) : 367–369 M/H, 1998.*
Bae Et Al Yakhak Hoechi 35(1): 7–10 Syn, 1991.*
Seo Et Al. Arch. Pharmacal. Res. 9(3):127–130 Syn, 1986.*
Bae Et Al Saengyak Hakhoechi 17(1)–85–90 Syn, 1986.*
Hattori Et Al Shoya Kusaku Zasshi: 39(1):76–79 Syn, 1985.*
Yoo Et Al Haksul Yongveah 8(2):207–212 M H, 1981.*
Ito Et Al Chem Pharm Bull 30(9):3347–3383 Syn, 1982.*
Dental Caries Prevention by Traditional Chinese Medicines—Part II—Potential Antibacterial Action of Magnoliae Cortex Extracts against *Streptococcus Mutans*, Journal of Medicinal Plant Research—1982, vol. 44, pp. 100–106.

* cited by examiner

*Primary Examiner*—Shep K. Rose
(74) *Attorney, Agent, or Firm*—Paul Shapiro

(57) ABSTRACT

An oral care composition containing a synergistic antiplaque/antigingivitis combination of a nonionic halogenated diphenyl ether compound such as Triclosan and an extract of Magnolia Officinalas containing honokiol and magnolol.

10 Claims, No Drawings

SYNERGISTIC ANTIPLAQUE/ANTIGINGIVITIS ORAL COMPOSITION

BACKGROUND OF THE INVENTION

1. Field of the Invention

This invention relates to a antiplaque combination of a noncationic halogenated hydroxydiphenyl ether antibacterial agent and an extract of Magnolia Officinalis and more particularly to an oral composition containing such combination which exhibits increased antigingivitis effect due to synergistic antibacterial effect against plaque bacteria.

2. The Prior Art

It is difficult to predict the antiplaque efficacy of antibacterial compounds when incorporated in a delivery vehicle and particularly in oral compositions. For example, dental plaque is a soft deposit which forms on teeth as opposed to calculus which is a hard calcified deposit on teeth. Unlike calculus, plaque may form on any part of the tooth surface, particularly at the gingival margin and is implicated in the occurrence of gingivitis. Cationic antibacterial compounds such as chlorhexidine, benzothonium chloride and cetyl pyridinium chloride have been used by the art as antibacterial antiplaque agents in oral compositions. However, such agents are generally not effective when there is also present in the oral composition an anionic surfactant required for the effective performance of oral compositions such as toothpaste and mouthrinses.

Noncationic antibacterial materials are compatible with anionic surfactants in oral compositions and noncationic halogenated hydroxydiphenyl ethers such as Triclosan have been effectively employed in commercial oral compositions as antiplaque agents when mixed with neutral ingredients such as humectants, abrasives and thickeners conventionally used in the formulation of oral compositions. Notwithstanding the efficacy of halogenated hydroxydiphenyl ethers such as Triclosan, there is a continuing interest in the oral care field for agents which improve the efficacy of such noncationic halogenated hydroxydiphenyl ethers.

Recently, interest has been displayed in the medicinal properties of herbal preparations for use in oral compositions. Herbal preparations are considered "more natural" and are therefore viewed as more acceptable antibacterial ingredients to the consumer.

Extracts of Magnolia Cortex (barks of Magnolia officinalis) are known to have antibacterial efficacy. For example, it has been reported in "Dental caries Prevention by Traditional Chinese Medicines", T. Namba et al, J. Medicinal Plant Res., vol. 44, pp. 100–106(1982) that some active principles of these extracts, identified to be magnolol and honokiol, were bactericidal against S. mutans in the in vitro test Minimal Inhibitory Concentration (MIC) but was not found to be inhibitory to plaque adherence to teeth in vitro tests designed to determine the therapeutic efficacy of antiplaque antigingivitis.

The dental art is continuously seeking synergistic enhancement of antiplaque/antigingivitis of non-herbal, antibacterial compositions such as halogenated biphenylether using herbal compositions in which the non-herbal ingredient has high antibacterial activity alone, while the herbal ingredient has little or no antiplaque activity, wherein the two ingredients have far higher antiplaque activity than could be expected from their individual activities, thus displaying synergism. The advantage of such synergism is that the effectiveness of the non-herbal antiplaque agent is greatly increased, without a concomitant increase in the dosage level or rate of administration so that lower quantities of the non-herbal antiplaque agent can be administered, yet still achieve the desired therapeutic effect. Such synergistic combinations are particularly important in the treatment of delicate or sensitive tissues, such as the oral mucosa, where the ability to reduce the level of the non-herbal antiplaque agent in the oral composition would be beneficial.

There is thus a recognized need for, and it would be highly advantageous to have a antiplaque dentifrice in which a combination of a non-herbal antiplaque agent and a herbal ingredient exhibited synergistic antiplaque activity resulting into enhanced effectiveness against gingivitis.

SUMMARY OF THE INVENTION

In accordance with the present invention it has been unexpectedly discovered that a combination of a nonionic halogenated hydroxydiphenyl ether such as Triclosan and phenolic compound selected from magnolol and honokiol and mixtures thereof extracted from the cortex of Magnolia Officinalas hereinafter referred to as "Magnolia Extract", are synergistically effective in inhibiting the growth of plaque causing bacteria whereby enhanced antiplaque activity in substantial excess of the additive antibacterial effect of the individual noncationic halogenated hydroxydiphenyl ether or Magnolia Extract is exhibited by the combination of these agents.

The fact that halogenated hydroxydiphenyl ether compounds such as Triclosan have been approved as safe and effective for use in oral care products and that the Magnolia Extract is a widely used herbal extract, particularly in Chinese medicine, suggests that these compounds will both be commercially acceptable as ingredients in oral hygiene products such as dentifrice, mouth rinse, chewing gum and lozenge formulations.

DETAILED DESCRIPTION OF THE PREFERRED EMBODIMENTS

The Magnolia Extract of the present invention is a dried cortex extract of Magnolia officinalis which belongs to the family Magnoliaceae. As used herein, "extracting" or "extraction" of a solid or liquid material means contacting the material, which if solid is preferably dried and crushed or ground, with an appropriate solvent to remove the substance(s) desired to be extracted from the material. Such an extraction may be carried out by conventional means; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

Preferred Magnolia Extracts used in the practice of the present invention are made from dried Magnolia plant bark and can be prepared by extracting the bark using an appropriate solvent. Preferred solvents include methanol, ethanol, methylene chloride, hexane cyclohexane, pentane, petroleum ether, chloroform and ethylene dichloride, one part of plant tissue (dry basis) is extracted with from about 5 to about 50 parts, preferably from about 15 parts to about 30 parts of solvent using an extraction apparatus where the solvent is contacted with the bark to obtain a concentrated paste which is then subjected to one or more additional extraction steps with different solvents to further concentrate the originally obtained paste over an extended period of time, preferably from about 6 hours to abut 1–2 days, more preferably for about 1 day.

In one method of extraction, the dried, crushed Magnolia bark in the form of a powder is sequentially contacted with ethanol, methylene chloride, and cyclohexane to form in each step a concentrated paste, the last paste form being dissolved in heated petroleum either at about 50°–60° C. and then dried under vacuum, the final extraction yielding an extract containing about 5 to about 10% by weight honokiol and about 15 to about 25% by weight magnolol.

Magnolol and honokiol are hydroxybiphenyl compounds, the structures of which being represented as follows:

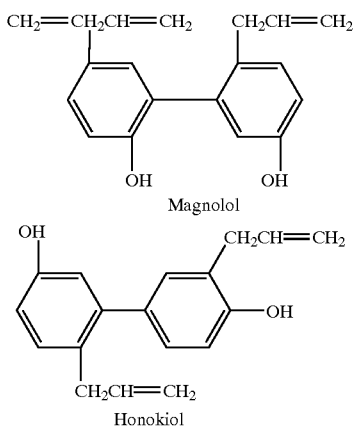

In the practice of the present invention, the antiplaque efficacy of an oral composition containing a noncationic antiplaque agent such as Triclosan, is synergistically enhanced by the presence in the oral composition of an amount of Magnolia Extract which will yield to the oral composition about 0.001 to about 50% by weight of magnolol and preferably about 0.01 to about 0.3 by weight and about 0.02 to about 0.1% by weight of honokiol and preferably about 0.024 to about 20% by weight.

These amounts of magnolol and honokiol are yielded to the oral composition when the Magnolia Extract about 1 to about 20% by weight of magnolol about 2 to about 50% by weight of honokiol.

Typical examples of noncationic halogenated diphenyl ethers which are particularly desirable from considerations of effectiveness, safety and formulation for use in synergistic combination with the Magnolia Extract are 2',4,4'trichloro-2-hydroxy-diphenyl ether (Triclosan) and 2,2'-dihydroxy-5,5'-dibromodiphenyl ether.

The synergistic antiplaque combination of Magnolia Extract and noncationic halogenated diphenyl ether may be administered to the oral cavity while dissolved or suspended in a pharmaceutically acceptable vehicle.

When the noncationic halogenated hydroxyphenyl ether is used in combination with Magnolia Extract to prepare oral compositions such as dentifrices and mouthrinses the sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Antitartar agents such as sodium tripolyphosphate, tetrapotassium or tetrasodium pyrophosphate, or mixtures thereof, can be present in the oral compositions of the present invention at concentrations from about 0.5 to about 8% by weight.

Agents used to diminish teeth sensitivity such as potassium chloride, potassium nitrate and potassium citrate can also be included in oral compositions of the present invention at concentrations of about 0.1 to about 10% by weight.

Various other materials may be incorporated in oral compositions of tis invention including preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the noncationlic halogenated hydroxyphenyl ether and hydrogenated lupulone antibacterial agent combination is dispersed in a mixture of ingredients, e.g. alcohol, humectants, surfactants, and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The antiplaque combination of this invention can be incorporated in lozenges, or in chewing gum or other products, e.g. by stirring into a warm gum base or coating the outer surface of a gum base, illustrative of which may be mentioned include jelutone, rubber latex and vinylite resins desirably with conventional plasticizers or softeners, sugar or other sweeteners or carbohydrates such as glucose, soxbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrozylate, hydrogenated glucose, hydrogenated disaccharides or hydrogenated polysaccharides, in an amount of about 90 to 98% by weight of the total composition. Salts such as sodium bicarbonate, sodium chloride, potassium bicarbonate or potassium chloride may totally or partially replace the polyol carrier. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following Examples further illustrate the present invention, but it is understood that the invention is not limited thereto. All amounts and proportions referred to

EXAMPLE I

A 0.3% solution in ethanol of Magnolia Extract containing 8% by weight honokiol and 21% by weight magnolol and a 0.3% by weight solution in ethanol of Triclosan were prepared, and the mixed solution at a 1:1 weight ratio designated "Composition 1" was evaluated in an MIC assay for bactericidal activity against S. mutans and F. nuceatum. The bacterial strain F. nuceatium is implicated in the occurrence of gingivitis.

MIC Assay

The bacterial strains of S. Mutans and F. nucteatum grown for 24 hours in trypticase soy broth and FTG* broth for 48 hours at 37° C. respectively to adjust its optical density between 0.1 and 0.2 absorption units at 610 nm prior to MIC determinations.

The Magnolia Extract and Triclosan solution mixture (Composition 1) was diluted and MIC assayed using the microtiter format according to standard procedures (Manual of Clinical Microbiology, 1995). The results are recorded in Table I below.

The FIC value (fractional inhibitory concentration) of Composition 1 was determined to assess whether the antibacterial efficacy of the Magnolia Extract Triclosan combination exhibited synergistic activity as is described in L. B. Quesnel et al in Journal of Applied Bacteriology, 1978, vol. 45, pages 397–405, L. O. Garrod et al in Antibiotic and Chemotherapy, pages 282–286 and 514–518.

$$FIC = \frac{MIC \text{ of Triclosan in mixture}}{MIC \text{ of Triclosan alone}} +$$

| $\frac{MIC \text{ of Magnolia Extract in mixture}}{MIC \text{ of Magnolia Extract alone}}$ | FIC | Implies |
|---|---|---|
| | $\leq 0.7$ | Synergism |
| | $1 +/- 0.3$ | Additive |
| | $\geq 1.3$ | Antagonistic |

The FIC value for the Magnolia Extract/Triclosan combination is recorded in Table I.

For purposes of comparison, individual 1% by weight solutions of Magnolia Extract, (designated "Composition C1") and Triclosan, (designated "Composition 2") were also subjected to MIC assay. The results are also recorded in Table I below.

TABLE I

| Composition No. | Solution | S. mutans | F. nucleatum |
|---|---|---|---|
| C1 | Magnolia Extract | 62.5 ± 0.0 | 31.3 ± 0.0 |
| C2 | Triclosan | 15.6 ± 0.0 | 2.0 ± 0.0 |
| 1 | Magnolia Extract + Triclosan | 7.8 ± 0.0 | 1.3 ± 0.6 |
| | FIC Composition 1 | 0.62 | 0.69 |

The results recorded in Table I show that Composition 1, the combination of the Magnolia Extract and Triclosan exhibit significantly greater bactericidal activity against S. mutans and F. nucleatum than would be expected from the additive effect of these materials. The FIC value for Composition 1 indicates an unexpected synergistic antibacterial activity against S. mutans and F. nucleatum.

EXAMPLE II

A dentifrice formulation (designated "Composition A") containing both Triclosan and a Magnolia Extract containing 8% by weight honokiol and 21% by weight manganol and the ingredients listed in Table II was prepared. A dentifrice having substantially same ingredients as Composition A except that the Magnolia Extract was not included in the dentifrice was used as a comparative composition and designated "Composition B". The ingredients of Compositions A and B are recorded in Table II below.

TABLE II

| Composition Ingredients | A Weight % | B Weight % |
|---|---|---|
| Di water | 16.107 | 15.807 |
| Glycerin | 20.00 | 20.00 |
| Carboxymethyl cellulose | 1.100 | 1.100 |
| Carrageenan | 0.400 | 0.400 |
| Sodium saccharin | 0.300 | 0.300 |
| Sodium fluoride | 0.243 | 0.243 |
| Titanium dioxide | 0.500 | 0.500 |
| Noncrystalizing sorbitol | 20.850 | 20.850 |
| Gantrez S-97 | 15.000 | 15.000 |
| Silica abrasive | 20.000 | 20.000 |
| Silica thickener | 1.500 | 1.500 |
| Flavor | 1.000 | 1.000 |
| Sodium hydroxide - 50% solution | 1.200 | 1.200 |
| Triclosan | 0.300 | 0.300 |
| Magnolia Extract | 0 | 0.300 |
| SLS | 1.500 | 1.500 |
| TOTAL | 100.000 | 100.000 |

In a six week study to monitor the effect of Composition A and comparative Composition B on gingivitis, 40 subjects were randomly assigned to one of two treatment groups, one group of subjects brushed their teeth twice daily with Composition A and the second group with Composition B. Product efficacy was clinically assessed using standard scoring methods. All subjects were examined professionally at baseline, three and six week intervals for presence of gingivitis according to the Gingival Index system a (G I, L oe 1967).

The scoring criteria was as follows:

Gingivital Inflammation

Score 0 Absence of inflammation

Score 1 Mild inflammation—slight change in color and little change in texture

Score 2 Moderate inflammation—moderate glazing, redness, edema and hypertrophy-bleeding on probing Score 3 Severe inflammation—marked redness and hypertrophy; tendency to spontaneous bleeding The GI score results are recorded in Table III as average/tooth/subject score.

TABLE III

| | | Gingival Index Scores | | | % Reduction | |
|---|---|---|---|---|---|---|
| | | | Elapsed Time | | | |
| Dentifrices | N | Base-line | 3 Weeks | 6 Weeks | v. Baseline | P |
| Composition A | 20 | 1.09 | 0.02 | 0.04 | 95% | P = 0.002 |
| Composition B | 20 | 1.11 | 0.67 | 0.58 | 47% | |

The results recorded in Table III indicate that the presence of the Magnolia Extract in the dentifrice composition produced a significant reduction in gingivitis by those subjects who brushed their teeth with Composition A.

What is claimed is:

1. An oral antigingivitis composition comprising an orally acceptable vehicle of a combination of a noncationic halogenated hydroxydiphenyl ether and an extract of Magnolia Cortex, the bark of Magnolia officinalis containing hydroxybiphenol compound selected from the group consisting of magnolol, honokiol, and mixtures thereof whereby plaque bacteria growth inhibition from the combination of the halogenated hydroxydiphenyl ether and hydroxybiphenol compounds exceeds the additive effect from the compounds if employed alone, the effective amount of the hydroxydiphenyl ether being in the range of about 0.003 to about 2% by weight and that of the Magnolia Extract being in the range of 0.001 to abut 10% by weight, and containing 2 to 50% by weight magnolol and 1 to 20% by weight honokiol.

2. The composition of claim 1 wherein the nonionic halogenated diphenyl ether compound is Triclosan.

3. The composition of claim 1 wherein the hydroxybiphenyl compounds are selected from magnolol, honokiol and mixtures thereof.

4. The composition of claim 1 wherein there is present in the composition a synthetic anionic polycarboxylate.

5. The composition of claim 4 wherein the polycarboxylate is a methyl vinyl ether/maleic anhydride copolymer.

6. A method of inhibiting the growth of plaque bacteria by contacting the bacteria with a composition comprising a pharmaceutically acceptable vehicle and an effective antiplaque amount of a combination of a noncationic halogenated hydroxydiphenyl ether and a Magnolia Extract containing hydroxybiphenyl compounds selected from the group consisting of magnolol, honokiol, and mixtures thereof whereby plaque bacteria growth inhibition from the combination of the halogenated hydroxydiphenyl ether and hydroxybiphenol compounds exceeds the additive effect from the compounds if employed alone, the effective amount of the hydroxydiphenyl ether being in the range of about 0.003 to about 2% by weight and that of the Magnolia Extract being in the range of 0.001 to about 10% by weight, and containing 2 to 50% by weight magnolol and 1 to 20% by weight honokiol.

7. The method of claim 6 wherein the nonionic halogenated diphenyl ether compound present in the composition is Triclosan.

8. The method of claim 6 wherein the hydroxybiphenyl compounds of the Magnolia extract present in the composition are selected from magnolol, honokiol and mixtures thereof.

9. The method of claim 6 wherein there is present in the composition a synthetic anionic polycarboxylate.

10. The composition of claim 9 wherein the polycarboxylate is a methyl vinyl ether/maleic anhydride copolymer.

* * * * *

UNITED STATES PATENT AND TRADEMARK OFFICE
CERTIFICATE OF CORRECTION

PATENT NO. : 6,500,409 B1
APPLICATION NO. : 09/568114
DATED : December 31, 2002
INVENTOR(S) : Scherl et al.

It is certified that error appears in the above-identified patent and that said Letters Patent is hereby corrected as shown below:

Delete column 1 line 1 to column 8 line 25 and insert column 1 line 1 to column 10 line 33 as attached.

Signed and Sealed this

Seventeenth Day of August, 2010

David J. Kappos
*Director of the United States Patent and Trademark Office*

US 6,500,409 B1

SYNERGISTIC ANTIPLAQUE/ANTIGINGIVITIS ORAL COMPOSITION

BACKGROUND OF THE INVENTION

1. Field of the Invention

This invention relates to a antiplaque combination of a noncationic halogenated hydroxydiphenyl ether antibacterial agent and an extract of Magnolia Officinalis and more particularly to an oral composition containing such combination which exhibits increased antigingivitis effect due to synergistic antibacterial effect against plaque bacteria.

2. The Prior Art

It is difficult to predict the antiplaque efficacy of antibacterial compounds when incorporated in a delivery vehicle and particularly in oral compositions. For example, dental plaque is a soft deposit which forms on teeth as opposed to calculus which is a hard calcified deposit on teeth. Unlike calculus, plaque may form on any part of the tooth surface, particularly at the gingival margin and is implicated in the occurrence of gingivitis. Cationic antibacterial compounds such as chlorhexidine, benzothonium chloride and cetyl pyridinium chloride have been used by the art as antibacterial antiplaque agents in oral compositions. However, such agents are generally not effective when there is also present in the oral composition an anionic surfactant required for the effective performance of oral compositions such as toothpaste and mouthrinses.

Noncationic antibacterial materials are compatible with anionic surfactants in oral compositions and noncationic halogenated hydroxydiphenyl ethers such as Triclosan have been effectively employed in commercial oral compositions as antiplaque agents when mixed with neutral ingredients such as humectants, abrasives and thickeners conventionally used in the formulation of oral compositions. Notwithstanding the efficacy of halogenated hydroxydiphenyl ethers such as Triclosan, there is a continuing interest in the oral care field for agents which improve the efficacy of such noncationic halogenated hydroxydiphenyl ethers.

Recently, interest has been displayed in the medicinal properties of herbal preparations for use in oral compositions. Herbal preparations are considered "more natural" and are therefore viewed as more acceptable antibacterial ingredients to the consumer.

Extracts of Magnolia Cortex (barks of Magnolia officinalis) are known to have antibacterial efficacy. For example, it has been reported in "Dental caries Prevention by Traditional Chinese Medicines", T. Namba et al, J. Medicinal Plant Res., vol. 44, pp. 100-106(1982) that some active principles of these extracts, identified to be magnolol and honokiol, were bactericidal against $S.$ $mutans$ in the in vitro test Minimal Inhibitory Concentration (MIC) but was not found to be inhibitory to plaque adherence to teeth in vitro tests designed to determine the therapeutic efficacy of antiplaque antigingivitis.

The dental art is continuously seeking synergistic enhancement of antiplaque/antigingivitis of non-herbal, antibacterial compositions such as halogenated biphenylether using herbal compositions in which the non-herbal ingredient has high antibacterial activity alone, while the herbal ingredient has little or no antiplaque activity, wherein the two ingredients have far higher antiplaque activity than could be expected from their individual activities, thus displaying synergism. The advantage of such synergism is that the effectiveness of the non-herbal antiplaque agent is greatly increased, without a concomitant increase in the dosage level or rate of administration so that lower quantities of the non-herbal antiplaque agent can be administered, yet still achieve the desired therapeutic effect. Such synergistic combinations are particularly important in the treatment of delicate or sensitive tissues, such as the oral mucosa, where the ability to reduce the level of the non-herbal antiplaque agent in the oral composition would be beneficial.

There is thus a recognized need for, and it would be highly advantageous to have a antiplaque dentifrice in which a combination of a non-herbal antiplaque agent and a herbal ingredient exhibited synergistic antiplaque activity resulting into enhanced effectiveness against gingivitis.

SUMMARY OF THE INVENTION

In accordance with the present invention it has been unexpectedly discovered that a combination of a nonionic halogenated hydroxydiphenyl ether such as Triclosan and phenolic compound selected from magnolol and honokiol and mixtures thereof extracted from the cortex of Magnolia Officinalas hereinafter referred to as "Magnolia Extract", are synergistically effective in inhibiting the growth of plaque causing bacteria whereby enhanced antiplaque activity in substantial excess of the additive antibacterial effect of the individual noncationic halogenated hydroxydiphenyl ether or Magnolia Extract is exhibited by the combination of these agents.

The fact that halogenated hydroxydiphenyl ether compounds such as Triclosan have been approved as safe and effective for use in oral care products and that the Magnolia Extract is a widely used herbal extract, particularly in Chinese medicine, suggests that these compounds will both be commercially acceptable as ingredients in oral hygiene products such as dentifrice, mouth rinse, chewing gum and lozenge formulations.

DETAILED DESCRIPTION OF THE PREFERRED EMBODIMENTS

The Magnolia Extract of the present invention is a dried cortex extract of Magnolia officinalis which belongs to the family Magnoliaceae. As used herein, "extracting" or "extraction" of a solid or liquid material means contacting the material, which if solid is preferably dried and crushed or ground, with an appropriate solvent to remove the substance(s) desired to be extracted from the material. Such an extraction may be carried out by conventional means; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such a by filtration or by settling and decanting.

Preferred Magnolia Extracts used in the practice of the present invention are made from dried Magnolia plant bark and can be prepared by extracting the bark using an appropriate solvent. Preferred solvents include methanol, ethanol, methylene chloride, hexane cyclohexane, pentane, petroleum ether, chloroform and ethylene dichloride, one part of plant tissue (dry basis) is extracted with from about 5 to about 50 parts, preferably from about 15 parts to about 30 parts of solvent using an extraction apparatus where the solvent is contacted with the bark to obtain a concentrated paste which is then subjected to one or more additional extraction steps with different solvents to further concentrate the originally obtained paste over an extended period of time, preferably from about 6 hours to about 1-2 days, more preferably for about 1 day.

In one method of extraction, the dried, crushed Magnolia bark in the form of a powder is sequentially contacted with ethanol, methylene chloride, and cyclohexane to form in each step a concentrated paste, the last paste form being dissolved in heated petroleum either at about 50°-60° C. and then dried under vacuum, the final extraction yielding an extract containing about 5 to about 10% by weight honokiol and about 15 to abut 25% by weight magnolol.

Magnolol and honokiol are hydroxybiphenyl compounds, the structures of which being represented as follows:

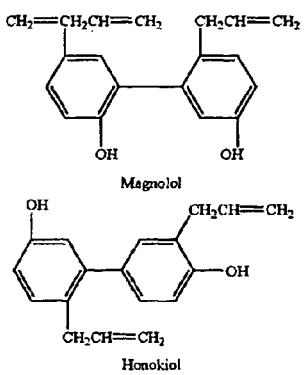

Magnolol

Honokiol

In the practice of the present invention, the antiplaque efficacy of an oral composition containing a noncationic antiplaque agent such as Triclosan, is synergistically enhanced by the presence in the oral composition of an amount of Magnolia Extract which will yield to the oral composition about 0.001 to about 50% by weight of magnolol and preferably about 0.01 to about 0.3 by weight and about 0.02 to about 0.1% by weight of honokiol and preferably about 0.024 to about 20% by weight.

These amounts of magnolol and honokiol are yielded to the oral composition when the Magnolia Extract about 1 to about 20% by weight of magnolol about 2 to about 50% by weight of honokiol.

Typical examples of noncationic halogenated diphenyl ethers which are particularly desirable from considerations of effectiveness, safety and formulation for use in synergistic combination with the Magnolia Extract are 2',4,4' trichloro-2-hydroxy-diphenyl ether (Triclosan) and 2,2'-dihydroxy-5,5'-dibromodiphenyl ether.

The synergistic antiplaque combination of Magnolia Extract and noncationic halogenated diphenyl ether may be administered to the oral cavity while dissolved or suspended in a pharmaceutically acceptable vehicle.

When the noncationic halogenated hydroxyphenyl ether is used in combination with Magnolia Extract to prepare oral compositions such as dentifrices and mouthrinses the halogenated hydroxyphenyl ether is incorporated in the oral composition in a non-toxic, effective amount, typically in a range of about 0.003 to about 2%, preferably about 0.02 to about 1% by weight.

To further enhance the synergistic antiplaque activity of the Magnolia Extract and halogenated hydrophenyl ether combination of the present invention, an antibacterial enhancing agent may be included in the oral composition. The use of such antibacterial enhancing agents in combination with noncationic antibacterial compounds is known to the art, as for example, U.S. Pat. Nos. 5,188,821 and 5,192,531.

Antibacterial enhancing agents preferred for use in the practice of the present invention include a natural or synthetic anionic polycarboxylates having a molecular weight of about 1,000 to about 5,000,000, preferably about 30,000 to about 500,000. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polycationic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B.F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4-5 million or more.

The antibacterial enhancing agent, when employed in the oral composition, is incorporated in the compositions in weight amounts of about 0.05 to about 5%, preferably about 0.1 to about 3%.

Fluoride ions may also be included in the oral compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt maybe used, but it is preferable to employ sufficient fluoride salt to release about 300 to 2,000 ppm, more preferably about 800 to about 1,500 ppm, of fluoride ion.

The oral composition of the present invention may be a solution of ingredients such as a mouthrinse or it maybe a semi-solid such as a toothpaste or gel dentifrice or chewing gum or solid lozenge.

In the aspect of this invention wherein the oral composition is a gel or paste, an orally acceptable vehicle, including a water-phase with humectant which is preferably glycerine or sorbitol an alkylene glycol such as polyethylene glycol or propylene glycol is present, wherein water is present typically in an amount of about 15-40% by weight and glycerine, sorbitol and/or the alkylene glycol (preferably propylene glycol) typically total about 20-75% by weight of the oral composition, more typically about 25-60% by weight.

When the oral composition is substantially semi-solid or pasty in character, such as a toothpaste or gel, the dentifrice vehicle may contain a dentally acceptable abrasive material such as sodium bicarbonate or water insoluble abrasive material such as sodium metaphosphate, potassium metaphosphate, tricalcium phosphate, dehydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10-30% by weight. Mouthrinses typically contain about 50-85% of water, about 0 to 20% by weight of a non-toxic alcohol and about 10-40% by weight of the humectant.

Surfactants are used in the compositions of the present invention to achieve increased prophylactic action and assist in the achieving thorough and complete dispersion of Triclosan and Magnolia Extract. The surfactant material is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Antitartar agents such as sodium tripolyphosphate, tetrapotassium or tetrasodium pyrophosphate, or mixtures thereof, can be present in the oral compositions of the present invention at concentrations from about 0.5 to about 8% by weight.

Agents used to diminish teeth sensitivity such as potassium chloride, potassium nitrate and potassium citrate can also be included in oral compositions of the present invention at concentrations of about 0.1 to about 10% by weight.

Various other materials may be incorporated in oral compositions of this invention including preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the noncationic halogenated hydroxyphenyl ether and hydrogenated lupulone antibacterial agent combination is dispersed in a mixture of ingredients, e.g. alcohol, humectants, surfactants, and flavor are then added and mixed. The ingredients are then mixed under vacuum for about 15-30 minutes. The resulting rinse product is then packaged. Dentifrices are prepared similarly, additional thickener and polishing agents being included in the last or penultimate step.

The antiplaque combination of this invention can be incorporated in lozenges, or in chewing gum or other products, e.g. by stirring into a warm gum base or coating the outer surface of a gum base, illustrative of which may be mentioned include jelutone, rubber latex and vinylite resins desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrozylate, hydrogenated glucose, hydrogenated disaccharides or hydrogenated polysaccharides, in an amount of about 90 to 98% by weight of the total composition. Salts such as sodium bicarbonate, sodium chloride, potassium bicarbonate or potassium chloride may totally or partially replace the polyol carrier. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following Examples further illustrate the present invention, but it is understood that the invention is not limited thereto. All amounts and proportions referred to herein and in the appended claims are by weight unless otherwise indicated.

EXAMPLE 1

A 0.3% solution in ethanol of Magnolia Extract containing 8% by weight honokiol and 21% by weight magnolol and a 0.3% by weight solution in ethanol of Triclosan were prepared, and the mixed solution at a 1:1 weight ratio designated "Composition 1" was evaluated in an MIC assay for bactericidal activity against $S.$ $mutans$ and $F.$ $nuceatum$. The bacterial strain $F.$ $nuceatium$ is implicated in the occurrence of gingivitis.

MIC ASSAY

The bacterial strains of $S.$ $Mutans$ and $F.$ $nucteatum$ grown for 24 hours in trypticase soy broth and FTG Fluid Thioglycolate* broth for 48 hours at 37° C. respectively to adjust its optical density between 0.1 and 0.2 absorption units at 610 nm prior to MIC determinations.

The Magnolia Extract and Triclosan solution mixture (Composition 1) was diluted and MIC assayed using the microtiter format according to standard procedures (Manual of Clinical Microbiology, 1995). The results are recorded in Table I below.

The FIC value (fractional inhibitory concentration) of Composition 1 was determined to assess whether the antibacterial efficacy of the Magnolia Extract Triclosan combination exhibited synergistic activity as is described in L. B. Quesnel et al in Journal of Applied Bacteriology, 1978, vol. 45, pages 397-405, L. O. Garrod et al in Antibiotic and Chemotherapy, pages 282-286 and 514-518.

$$FIC = \frac{MIC \text{ of Triclosan in mixture}}{MIC \text{ of Triclosan alone}} +$$

| $\frac{MIC \text{ of Magnolia Extract in mixture}}{MIC \text{ of Magnolia Extract alone}}$ | FIC | Implies |
|---|---|---|
| | <=0.7 | Synergism |
| | 1 +/- 0.3 | Additive |
| | >=1.3 | Antagonistic |

The FIC value for the Magnolia Extract/Triclosan combination is recorded in Table I.

For purposes of comparison, individual 1% by weight solutions of Magnolia Extract, (designated "Composition C1") and Triclosan, (designated "Composition 2") were also subjected to MIC assay. The results are also recorded in Table I below.

TABLE I

| Composition No. | Solution | S. mutans | F. nucleatum |
|---|---|---|---|
| C1 | Magnolia Extract | 62.5 ± 0.0 | 31.3 ± 0.0 |
| C2 | Triclosan | 15.6 ± 0.0 | 2.0 ± 0.0 |

TABLE I-continued

| Composition No. | Solution | S. mutans | F. nucleatum |
|---|---|---|---|
| 1 | Magnolia Extract + Triclosan | 7.8 ± 0.0 | 1.3 ± 0.6 |
| | FIC Composition 1 | 0.62 | 0.69 |

The results recorded in Table I show that Composition 1, the combination of the Magnolia Extract and Triclosan exhibit significantly greater bactericidal activity against $S.$ $mutans$ and $F.$ $nucleatum$ than would be expected from the additive effect of these materials. The FIC value for Composition 1 indicates an unexpected synergistic antibacterial activity against $S.$ $mutans$ and $F.$ $nucleatum$.

EXAMPLE II

A dentifrice formulation (designated "Composition A") containing both Triclosan and a Magnolia Extract containing 8% by weight honokiol and 21% by weight manganol and the ingredients listed in Table II was prepared. A dentifrice having substantially same ingredients as Composition A except that the Magnolia Extract was not included in the dentifrice was used as a comparative composition and designated "Composition B". The ingredients of Compositions A and B are recorded in Table II below.

TABLE II

| Composition Ingredients | A Weight % | B Weight % |
|---|---|---|
| Di water | 16.107 | 15.807 |
| Glycerin | 20.00 | 20.00 |
| Carboxymethyl cellulose | 1.100 | 1.100 |
| Carrageenan | 0.400 | 0.400 |
| Sodium saccharin | 0.300 | 0.300 |
| Sodium fluoride | 0.243 | 0.243 |
| Titanium dioxide | 0.500 | 0.500 |
| Noncrystalizing sorbitol | 20.850 | 20.850 |
| Gantrez S-97 | 15.000 | 15.000 |
| Silica abrasive | 20.000 | 20.000 |
| Silica thickener | 1.500 | 1.500 |
| Flavor | 1.000 | 1.000 |
| Sodium hydroxide-50% solution | 1.200 | 1.200 |
| Triclosan | 0.300 | 0.300 |
| Magnolia Extract | 0 | 0.300 |
| SLS | 1.500 | 1.500 |
| TOTAL | 100.000 | 100.000 |

In a six week study to monitor the effect of Composition A and comparative Composition B on gingivitis, 40 subjects were randomly assigned to one of two treatment groups, one group of subjects brushed their teeth twice daily with Composition A and the second group with Composition B. Product efficacy was clinically assessed using standard scoring methods. All subjects were examined professionally at baseline, three and six week intervals for presence of gingivitis according to the Gingival Index system (GI, Löe 1967).

The scoring criteria was as follows:
Gingivital Inflammation
Score 0 Absence of inflammation
Score 1 Mild inflammation—slight change in color and little change in texture
Score 2 Moderate inflammation—moderate glazing, redness, edema and hypertrophy-bleeding on probing
Score 3 Severe inflammation—marked redness and hypertrophy; tendency to spontaneous bleeding
The GI score results are recorded in Table III as average/tooth/subject score.

TABLE III

Gingival Index Scores

| Dentrifices | N | Baseline | Elapsed Time 3 Weeks | Elapsed Time 6 Weeks | % Reduction v. Baseline | P |
|---|---|---|---|---|---|---|
| Composition A | 20 | 1.09 | 0.02 | 0.04 | 95% | P = 0.002 |
| Composition B | 20 | 1.11 | 0.67 | 0.58 | 47% | |

The results recorded in Table III indicate that the presence of the Magnolia Extract in the dentifrice composition produced a significant reduction in gingivitis by those subjects who brushed their teeth with Composition A.

What is claimed is:

1. An oral antigingivitis composition comprising an orally acceptable vehicle of a combination of a noncationic halogenated hydroxydiphenyl ether and an extract of Magnolia Cortex, the bark of *Magnolia officinalis* containing hydroxybiphenol compound selected from the group consisting of magnolol, honokiol, and mixtures thereof whereby plaque bacteria growth inhibition from the combination of the halogenated hydroxydiphenyl ether and hydroxybiphenol compounds exceeds the additive effect from the compounds if employed alone, the effective amount of the hydroxydiphenyl ether being in the range of about 0.003 to about 2% by weight and that of the Magnolia Extract being in the range of 0.001 to abut 10% by weight, and containing 2 to 50% by weight magnolol and 1 to 20% by weight honokiol.

2. The composition of claim 1 wherein the nonionic halogenated diphenyl ether compound is Triclosan.

3. The composition of claim 1 wherein the hydroxybiphenyl compounds are selected from magnolol, honokiol and mixtures thereof.

4. The composition of claim 1 wherein there is present in the composition a synthetic anionic polycarboxylate.

5. The composition of claim 4 wherein the polycarboxylate is a methyl vinyl ether/maleic anhydride copolymer.

6. A method of inhibiting the growth of plaque bacteria by contacting the bacteria with a composition comprising a pharmaceutically acceptable vehicle and an effective antiplaque amount of a combination of a noncationic halogenated hydroxydiphenyl ether and a Magnolia Extract containing hydroxybiphenyl compounds selected from the group consisting of magnolol, honokiol, and mixtures thereof whereby plaque bacteria growth inhibition from the combination of the halogenated hydroxydiphenyl ether and hydroxybiphenol compounds exceeds the additive effect from the compounds if employed alone, the effective amount of the hydroxydiphenyl ether being in the range of about 0.003 to about 2% by weight and that of the Magnolia Extract being in the range of 0.001 to about 10% by weight, and containing 2 to 50% by weight magnolol and 1 to 20% by weight honokiol.

7. The method of claim 6 wherein the nonionic halogenated diphenyl ether compound present in the composition is Triclosan.

8. The method of claim 6 wherein the hydroxybiphenyl compounds of the Magnolia extract present in the composition are selected from magnolol; honokiol and mixtures thereof.

9. The method of claim 6 wherein there is present in the composition a synthetic anionic polycarboxylate.

10. The composition of claim 9 wherein the polycarboxylate is a methyl vinyl ether/maleic anhydride copolymer.

* * * * *